(12) United States Patent
Garst

(10) Patent No.: US 8,716,238 B2
(45) Date of Patent: May 6, 2014

(54) CYCLOSPORIN DERIVATIVES FOR TREATING OCULAR AND DERMAL DISEASES AND CONDITIONS

(75) Inventor: Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 924 days.

(21) Appl. No.: 12/499,911

(22) Filed: Jul. 9, 2009

(65) Prior Publication Data

US 2010/0009953 A1     Jan. 14, 2010

Related U.S. Application Data

(60) Provisional application No. 61/134,510, filed on Jul. 10, 2008.

(51) Int. Cl.
*A61K 38/13* (2006.01)

(52) U.S. Cl.
USPC ........................................................ 514/20.5

(58) Field of Classification Search
USPC ........................................................ 514/20.5
See application file for complete search history.

(56) References Cited

U.S. PATENT DOCUMENTS

| | | | |
|---|---|---|---|
| 4,649,047 | A | 3/1987 | Kaswan |
| 5,474,979 | A | 12/1995 | Ding et al. |
| 5,948,755 | A | 9/1999 | Barriere et al. |
| 5,965,527 | A | 10/1999 | Barriere et al. |
| 5,994,299 | A | 11/1999 | Barriere et al. |
| 6,254,860 | B1 | 7/2001 | Garst |
| 6,350,442 | B2 | 2/2002 | Garst |

FOREIGN PATENT DOCUMENTS

| | | | |
|---|---|---|---|
| WO | WO99-65933 | | 12/1999 |
| WO | WO 00/61168 | | 10/2000 |
| WO | WO03-051797 | | 6/2003 |
| WO | WO 2010/006117 | * | 1/2010 |

OTHER PUBLICATIONS

Kaswan et al, Am. J. Vet. Res. 46, pp. 376-383, 1985.
Georgala et al, "Pimecrolimus 1% Cream in Non-Specific inflammtory Recurrent Balanitis", Dermatology. 215, pp. 209-212, 2007.
Salek et al, "Cyclosporin Greatly Improves the Quality of Life of Adults with Severe Atropic Dermatitis. A Randomized, Double-Bind, Placebo Controlled Trial", Br. J. Drmatol, 129, pp. 422-430, 1993.
Dieter Seebach, Modification of Cyclosporin A (CS): Generation of an Enolate at Thesarcosine Residue and Reactions with Electrophiles, Helvetica Chimica, 1993, 1564-1590, 76 (4).

* cited by examiner

*Primary Examiner* — Zohreh Fay
(74) *Attorney, Agent, or Firm* — Jennifer C. Cheng; Joel B. German; Debra D. Condino

(57) ABSTRACT

The present invention provides a method for the treatment of ocular or dermal diseases and/or conditions, e.g. an aqueous deficient dry eye state, uveitis or phacoanaphylactic endophthalmitis in an eye, or balanitis, psoriasis, or atopic dermatitis of the skin, said method comprising administering, topically to the eye or the skin, a therapeutically effective amount of a novel cyclosporin A derivative selected from the group consisting of compounds represented by the formula:

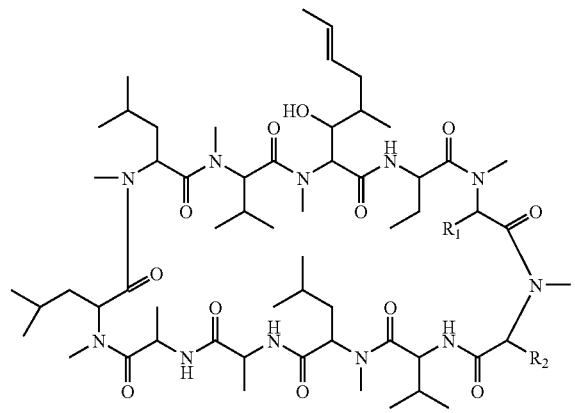

wherein $R_1$ is S-Alk-R wherein Alk is an alkylene linkage, preferably a methylene or poly methylene linkage, e.g. a $C_2$ to $C_6$ polymethylene linkage, or a polyalkenylene linkage, e.g. a $C_3$ to $C_6$ alkenylenyl linkage, R is R is —N=C(NR$_3$R$_4$)(NR$_5$R$_6$) or
—NR$_7$[(NR$_3$R$_4$)C=NR$_5$], i.e. guanidines or
—N=C(R$_8$)(NR$_9$R$_{10}$), i.e. amidines wherein R$_3$-R$_{10}$ is H, Alk, Ar or (CH$_2$)nAr wherein Ar is an aryl group and n is an integer of from 1 to 13 or R$_3$ and R$_4$ or R$_4$ and R$_5$ or R$_5$ and R$_7$ or R$_3$ and R$_7$, or R$_9$ and R$_{10}$, together may be —CH$_2$—CH$_2$— or —CH$_2$—CH$_2$—CH$_2$— and R$_2$ is selected from the group consisting of hydroxyl, lower alkyl and hydroxyl-substituted lower alkyl and R$_2$ is selected from the group consisting of hydroxy and lower alkyl.

6 Claims, No Drawings

CYCLOSPORIN DERIVATIVES FOR TREATING OCULAR AND DERMAL DISEASES AND CONDITIONS

CROSS REFERENCE TO RELATED PATENT APPLICATIONS

This Patent Application is related to U.S. Provisional Patent Application No. 61/134,510, which is entitled Cyclosporin Derivatives For Treating Ocular And Dermal Diseases And Conditions and was filed on Jul. 10, 2008.

BACKGROUND OF THE INVENTION

1. Field of the Invention

The invention relates to a method of treating ocular and/or dermal diseases and conditions with novel cyclosporine derivatives. In particular, the present invention relates to a method for the treatment of aqueous deficient dry-eye state, phacoanaphylaxis endophthalmitis and uveitis using certain novel cyclosporine derivatives.

2. Description of the Related Art

The exposed part of a normal eye is covered by a thin tear film. The presence of a continuous tear film is important for the well-being of the corneal and conjunctival epithelium and provides the cornea with an optically high quality surface. In addition, the aqueous part of the tear film acts as a lubricant to the eyelids during blinking of the lids. Furthermore, certain enzymes contained in the tear fluid, for example immunoglobin A, lysozyme and beta lysin, are known to have bacteriostatic properties.

A sound lacrimal system functions to form and maintain a properly structured, continuous tear film. The lacrimal apparatus consists of the secretory system (the source), the distribution system, and the excretory system (the sink). In the secretory system, aqueous tears are supplied by main and accessory lacrimal glands.

The bulk of the tear film is made of such aqueous tear. The continuous production and drainage of aqueous tear is important in maintaining the corneal and conjunctival epithelium in a moist state, in providing nutrients for epithelial respiration, in supplying bacteriostatic agents and in cleaning the ocular surface by the flushing action of tear movement.

Abnormalities of the tear film include an absolute or partial deficiency in aqueous tear production (keratoconjunctivitis sicca, or KCS).

In relatively mild cases, the main symptom of KCS is a foreign body sensation or a mild scratchiness. This can progress to become a constant, intense burning or irritative sensation that can be debilitating to a patient.

More severe forms can progress to the development of filamentary keratitis, a painful condition characterized by the appearance of numerous strands or filaments attached to the corneal surface. Evidence suggests that these filaments represent breaks in the continuity of normal corneal epithelial cells. The shear created by lid motion pulls these filaments, causing pain. Management of this stage of KCS is very difficult.

A frequent complication of KCS is secondary infection. Several breakdowns in the eye's normal defense mechanisms seem to occur, presumably attributable to a decrease in the concentration of antibacterial lysozyme in the aqueous tears of a patient suffering from KCS.

Although KCS can develop in the absence of any other overt system abnormality, there is a frequent association of KCS with systemic disease. KCS can occur as part of a larger systemic involvement known as Sjogren's syndrome. This classically consists of dry eyes, dry mouth and arthritis.

Histologically, in KCS (as part of Sjogren's syndrome or in isolation), the initial changes seen in the lacrimal glands are those of focal lymphocytic and plasma cell infiltrates associated with degeneration of glandular tissue. These changes resemble those seen in autoimmune disease in other tissue, giving rise to the speculation that KCS has an autoimmune basis.

Sjogren's syndrome is recognized as an exocrine gland dysfunction. Characteristically, the lacrimal glands show a mononuclear cell infiltration that ultimately leads to destruction of the glandular structure.

Conventional treatment of KCS is symptomatic. Normally, aqueous-deficient dry eye states are treated by supplementation of the tears with artificial tear substitutes. However, relief is limited by the retention time of the administered artificial tear solution in the eye. Typically, the effect of an artificial tear solution administered to the eye dissipates within about thirty to forty-five minutes. Thus, the effect of such products, while soothing initially, does not last long enough. The patient is inconvenienced by the necessity of repeated administration of artificial tear solution in the eye as needed to supplement the normal tears. Moreover, such treatment merely acts to alleviate the symptoms of the dry eye state and does not cure any underlying disorders or causes of the dry eye state.

Histologic studies of the lacrimal glands in patients suffering from Sjogren's syndrome have shown some evidence of lacrimal gland inflammation. Such inflammation may be simply due to the normal aging of the patient. It has been suggested that the use of anti-inflammatory agents might serve to decrease the glandular inflammation. The systemic use of corticosteroids has been advocated in these conditions. However, the merit of systemic corticosteroids in dry eye states has not been established. In most dry eye cases, the hazards of long-term use of anti-inflammatory agents would seem to outweigh their potential merit.

Surgical procedures have also been suggested in the management of dry eye states. Where there has been significant conjunctival destruction, mucous membrane transplants have been advocated. It has also been suggested that parotid (saliva) duct transplantation can be useful in the management of dry eyes. However, surgical alterations to combat dry eye conditions constitute a dramatic remedy and any benefit resulting from these alterations is questionable.

It has also been suggested to administer orally a dilute solution of pilocarpine to stimulate the autonomic nervous system to effect increased aqueous tear production. This method of treatment has not met with universal favor because of many unpleasant side effects of ingested pilocarpine.

Animal models of Sjogren's syndrome have been instrumental in basic ophthalmic research. A Sjogren's-like disease has been found in dogs with systemic luperythematosus. This disease, which may be referred to as canine KCS, is a common, chronic, progressive, and potentially blinding disease. A continuum of corneal and conjunctival lesions ensues from the dry eye state. The cause of canine KCS is often not identified. Usually canine KCS is not an isolated ophthalmic disease. It has been speculated in Kaswan et al., Am. J. Vet. Res. 46, 376-383 (1985), that most cases of canine KCS occur via autoimmune mechanisms.

Other diseases of the eye include phacoanaphylactic endophthalmitis and uveitis. These diseases can be located throughout the eye, in both the posterior and anterior chambers of the eye as well as in the vitreous body.

Uveitis, the inflammation of the uvea, is responsible for about 10% of the visual impairment in the United States. Phacoanaphylactic endophthalmitis is a human autoimmune disease.

Panuveitis refers to inflammation of the entire uveal (vascular) layer of the eye. Posterior uveitis generally refers to chorioentinitis, and anterior uveitis refers to iridocyclitis. The inflammatory products (i.e. cells, fibrins, excess proteins) of these inflammations are commonly found in the fluid spaces if the eye, i.e. anterior chamber, posterior chamber and vitreous space as well as infiltrating the tissue intimately involved in the inflammatory response. Uveitis may occur following surgical or traumatic injury to the eye; as a component of an autoimmune disorder, i.e. rheumatoid arthritis, Behcet's disease, ankylosing spondylitis, sarcoidosis; as an isolated immune mediated ocular disorder, i.e. pars planitis, iridocyclitis etc., unassociated with known etiologies; and following certain systemic diseases which cause antibody-antigen complexes to be deposited in the uveal tissues. Together these disorders represent the non-infectious uveitities.

The normal eye is protected from immune surveillance by blood barriers which do not allow free migration of cells or proteins into the eye. When the eye is injured or when vasculitis occurs, the internal ocular structures are exposed to the general immune system and frequently illicit autoinmmune responses.

The compounds of this invention are also useful in treating dermal diseases and conditions. It has been found that the compounds of this invention may be used to treat balanitis, e.g. non-specific inflammatory recurrent balanitis. See "Pimecrolimus 1% Cream in Non-Specific Inflammatory Recurrent Balanitis" by S. Georgala, et al., *Dermatology* 2007; 215:209-212. The compounds of this invention may be used to treat psoriasis and atopic dermatitis. (See "Cyclosporin Greatly Improves the Quality of Life of Adults with Severe Atopic Dermatitis. A Randomized, Double-Bind, Placebo Controlled Trial" by M S Salek, et al., *Br J Drmatol* 1993: 129:422-430 and Physicians' Desk Reference: PDR-Gengraf Capsules (Abbot), respectively.)

Phacoanaphylaxis is a severe form of uveitis in which the lens in the causative antigen. The lens proteins are normally secluded by the lens capsule since before birth. When these proteins are released into the eye by injury or by surgery or occasionally during cataract development, they can become intensely antigenic and incite an autoimmune response. If the response is moderate it is seen as chronic uveitis. If it is very fast in progression the eye becomes seriously inflamed in all segments. This latter response is named phacoanaphylaxis.

Methylthio-substituted cyclosporin A and other alkylthio-substituted cyclosporin A derivatives have been described in PCT application Nos. 98-379455, 98-379456 and 98-379457 and have been found to be active against certain retroviruses, especially AIDS (acquired immunodeficiency syndrome) and ARC (AIDS-related complex) when administered orally, parenterally, rectally or by inhalation. In addition, they have generally been found to have only a very weak immunosuppressant action, and to show anti-retroviral activity at non-cytotoxic and non-cytostatic concentrations. These compounds are claimed to have a synergistic action with other agents active against retrovirus (such as inhibitors of reverse transcriptase, protease, integrase, HIV replication and nucleocapside).

These compounds are also claimed for use in the treatment of ocular diseases and conditions in U.S. Pat. Nos. 6,350,442 and 6,254,860.

It is one object of this invention to provide novel cyclosporine A derivatives to treat ocular diseases and conditions, such as dry eye.

It is another object of the invention to provide new cyclosporine A derivatives

It is another object of the invention to treat dermal diseases and/or conditions, such as balanitis.

It is another object of the invention to treat dermal conditions, such as psoriasis and atopic dermatitis.

Other objects of this invention will become apparent from a reading of the present specification.

SUMMARY OF THE INVENTION

The present invention provides a method for treating an ocular disorder or condition of the eye, for example, an aqueous deficient dry eye state, uveitis, or phacoanaphylactic endophthalmitis, comprising the step of administering to an eye, a therapeutically effective amount of a compound selected from the group consisting of cyclosporin A derivatives of the formula described below. The present invention provides a method for treating a dermal disorder or condition of the skin, for example, balanitis, or psoriasis, or atopic dermatitis, comprising the step of administering to an eye, a therapeutically effective amount of a compound selected from the group consisting of cyclosporin A derivatives. The cyclosporin A derivatives utilized in the method(s) of the present invention are represented by the formula

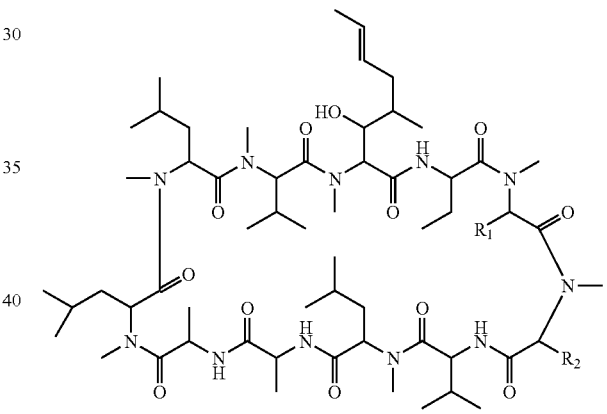

wherein $R_1$ is S-Alk-R wherein Alk is an alkylene linkage, preferably a methylene or poly methylene linkage, e.g. a $C_2$ to $C_6$ polymethylene linkage, or a polyalkenylene linkage, e.g. a $C_3$ to $C_6$ alkenylenyl linkage and R is $-N=C(NR_3R_4)(NR_5R_6)$ or $-NR_7[(NR_3R_4)C=NR_5]$, i.e. guanidines or $-N=C(R_8)(NR_9R_{10})$, i.e. amidines wherein $R_3$-$R_{10}$ is H, Alk, Ar or $(CH_2)$nAr wherein Ar is an aryl group and n is an integer of from 1 to 13 or $R_3$ and $R_4$, or $R_4$ and $R_5$, or $R_5$ and $R_7$, or $R_3$ and $R_7$, or $R_9$ and $R_{10}$, or $R_8$ and $R_9$, together, may be $-(CH_2)_x-$, wherein x is an integer of from 2 to 5, e.g. $-CH_2-CH_2-$ or $-CH_2-CH_2-CH_2-$ and $R_2$ is selected from the group consisting of hydroxyl, lower alkyl and hydroxyl-substituted lower alkyl. For example, $R_1$ may be $-S(CH_2)_2N=C(NH_2)_2$ and $R_2$ may be $-CH_2CH(CH_3)_2$, $-CH_2C(OH)(CH_3)_2$, $-CH(CH_3)_2$ or $-CH(CH_3)CH_2CH_3$.

DETAILED DESCRIPTION OF THE INVENTION

The present invention provides a method for the treatment of uveitis and phacoanaphylactic endophthalmitis, in a patient suffering therefrom, as well as an aqueous deficient dry eye state, by topical application to the affected eye, of a cyclosporin derivative, represented by the formula below

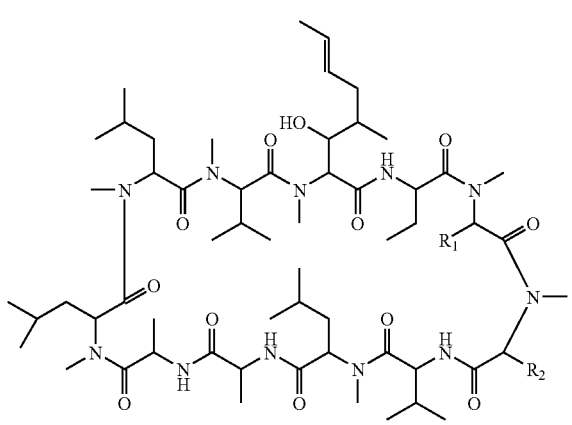

wherein $R_1$ is S-Alk-R wherein Alk is an alkylene linkage, preferably a methylene or poly methylene linkage, e.g. a $C_2$ to $C_6$ polymethylene linkage, or a polyalkenylene linkage, e.g. a $C_3$ to $C_6$ alkenylenyl linkage and R is —N=C($NR_3R_4$)($NR_5R_6$) or —$NR_7$[($NR_3R_4$)C=$NR_5$], i.e. guanidines or —N=C($R_8$)($NR_9R_{10}$), i.e. amidines wherein $R_3$-$R_{10}$ is H, Alk, Ar or ($CH_2$)nAr wherein Ar is an aryl group and n is an integer of from 1 to 13 or $R_3$ and $R_4$ or $R_4$ and $R_5$ or $R_5$ and $R_7$ or $R_3$ and $R_7$, or $R_9$ and $R_{10}$, together may be —$CH_2$—$CH_2$— or —$CH_2$—$CH_2$—$CH_2$— and $R_2$ is selected from the group consisting of hydroxyl, lower alkyl and hydroxyl-substituted lower alkyl. R is —N=C($NR_3R_4$)($NR_5R_6$) or —$NR_7$C($NR_3$)(C=$NR_5$), wherein $R_3$-$R_7$ is H, Alk, Ar or ($CH_2$)nAr wherein Ar is an aryl group, e.g. a carbocyclic aryl or a heterocyclic aryl, and n is an integer of from 1 to 13, e.g. an integer of from 1 to 4, or $R_3$ and $R_4$, or $R_4$ and $R_5$, or $R_5$ and $R_7$, or $R_3$ and $R_7$, or $R_9$ and $R_{10}$, or $R_8$ and $R_9$, together, may be may be —($CH_2$)$_x$—, wherein x is an integer of from 2 to 5, e.g. —$CH_2$—$CH_2$— or —$CH_2$—$CH_2$—$CH_2$— and $R_2$ is selected from the group consisting of hydroxy and lower alkyl.

For the purpose of describing and claiming the present invention the following terms shall have the following meanings:

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino and SH.

"Alkenyl" refers to a straight-chain, branched or cyclic unsaturated hydrocarbon group containing at least one carbon-carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, O, S, $NO_2$, halogen, dimethyl amino and SH.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Alkoxy" refers to an "O-alkyl" group.

"tBoc" refers to a t-butyloxycarbonyl protecting group.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen.

The cyclosporine A derivatives used in the method of this invention are prepared as follows:

Compounds where $R_4$, $R_5$ and $R_6$ are hydrogen and $R_7$ is hydrogen, alkyl, substituted alkyl or aryl may be prepared by reaction of a compound of formula (I) where X is a leaving group and P is a protecting group with a compound of formula (II) in a suitable solvent such as methanol to afford compounds of formula (III). For compounds of formula I, typical examples of the protecting group are where X=chlorine, MeS, MeSO2, 1-imidazolyl and especially 1-pyrazolyl. Protecting groups P are preferably tertiary butyloxycarbonyl groups (tBoc) groups.

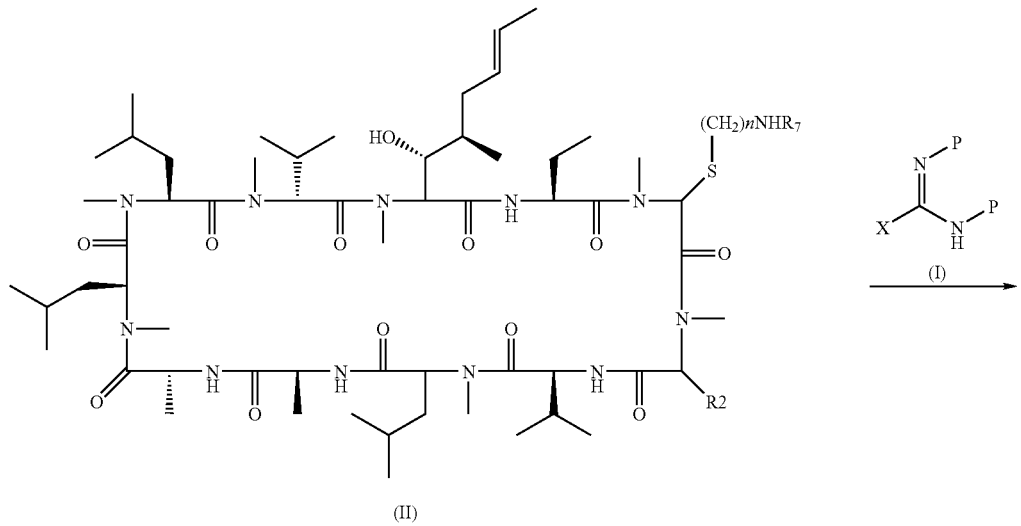

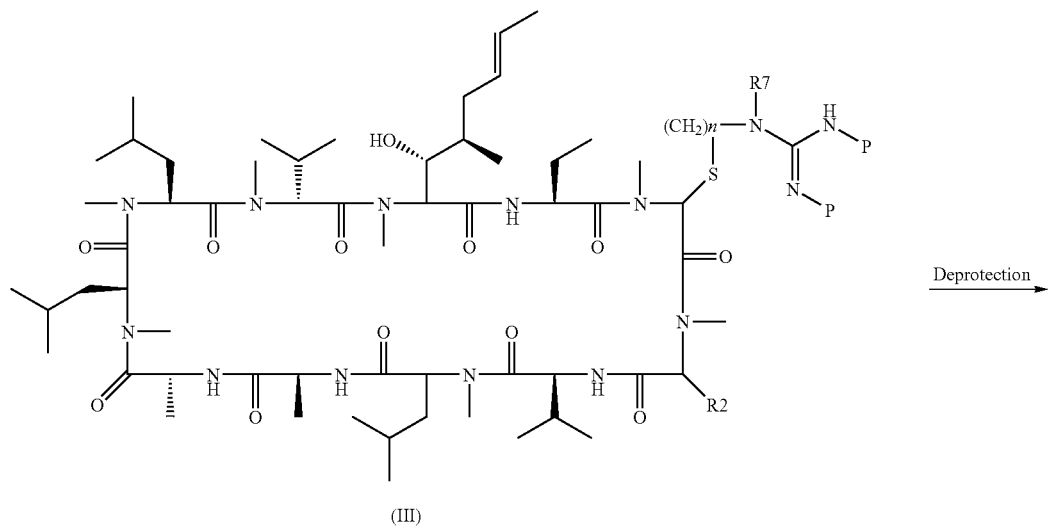

(III)

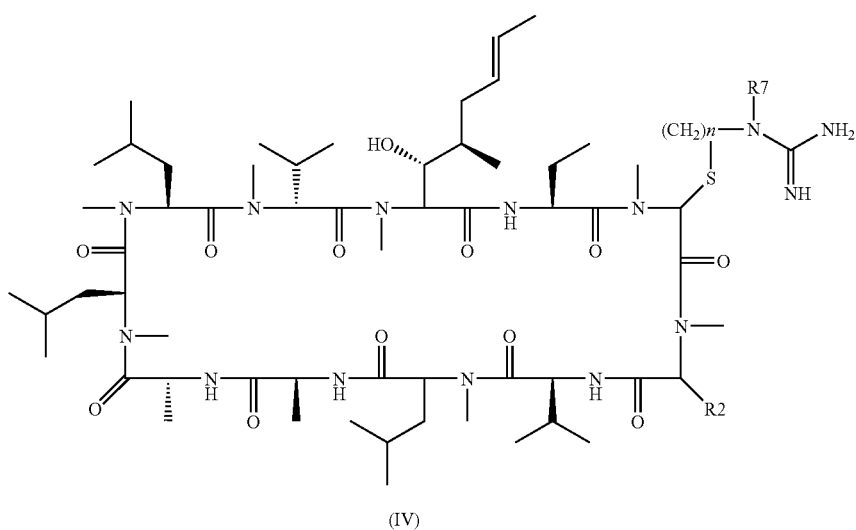

(IV)

Compounds of formula (III) may be de-protected under a variety of conditions to provide compounds of formula (IV). For example, when P=tertiary butyloxycarbonyl groups (tBoc), this may be removed under acidic conditions using acids such as methanesulphonic acid.

Compounds of formula (V) where $R_7$ is hydrogen, alkyl, substituted alkyl or aryl; $R_3$ is alkyl, substituted alkyl or aryl, may be prepared by reaction of a compound of formula (VI) where X is a leaving group and P is a protecting group with a compound of formula (II) in a suitable solvent such as methanol to afford compounds of formula (VII).

For compounds of formula (VI), typical examples of the protecting group are where X=chlorine, MeS, MeSO2, 1-imidazolyl and especially 1-pyrazolyl. Protecting groups P are preferably tertiary butyloxycarbonyl groups (tBoc) groups.

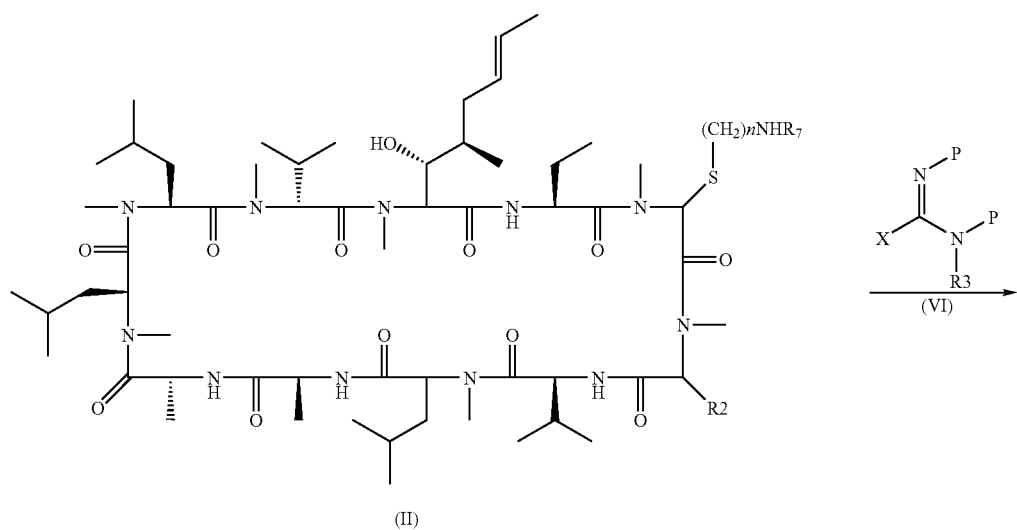
(II)
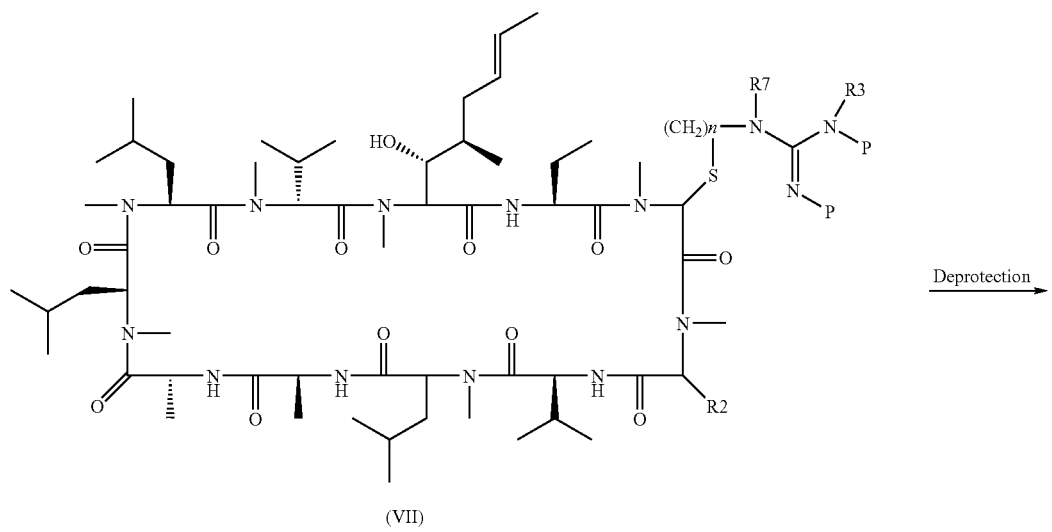
(VII)
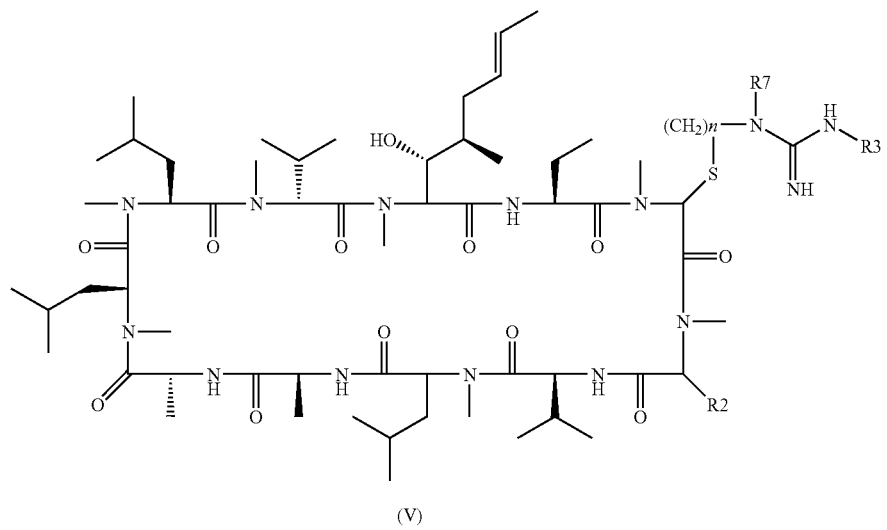
(V)

For example, in WO/2003/051797 N,N'-Di-tBoc-N-methyl-1H-pyrazole-1-carboxamidine has been used to prepare an N-methyl guanidine in an unrelated chemical family.

Other compounds of the invention may be made in similar ways using related synthetic methods with, if appropriate, suitable protecting groups compatible with the synthetic methodology.

Compounds of formula (X) where R is $-N=C(R_8)-NR_9R_{10}$ (amidines) where $R_8$ is hydrogen, alkyl, substituted alkyl or aryl and $R_9$ and $R_{10}$ can be alkyl, substituted alkyl or aryl or $R_9$ and $R_{10}$ can form a ring may be prepared by reaction of a compound of formula (VIII) with a compound of formula (IX) to afford compounds of formula (X). $R_{11}$ is preferably lower alkyl and typical examples of compound (VIII) are Dimethylformamide dimethylacetal (DMF.DMA) and Dimethylacetamide dimethylacetal (DMA.DMA).

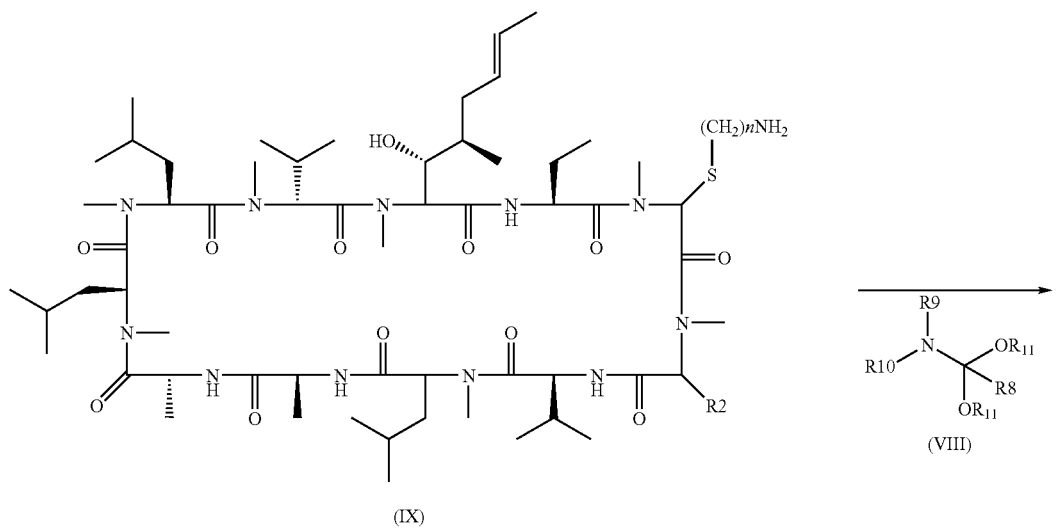

(IX)

(VIII)

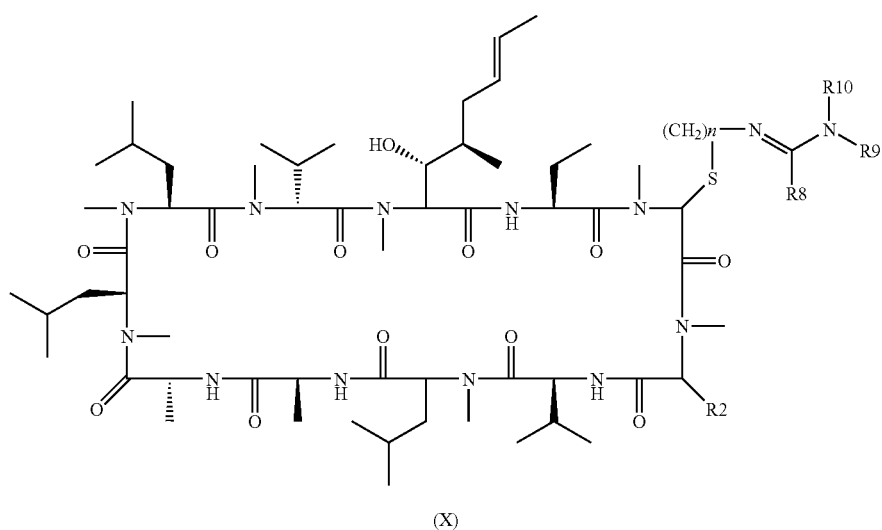

(X)

Below are specific examples of the preparation of certain compounds of the invention by the above general procedures.
Guanidine and Amidine Analogues of 3-[(2-aminoethylthio]-cyclosporin A
EXAMPLE 1
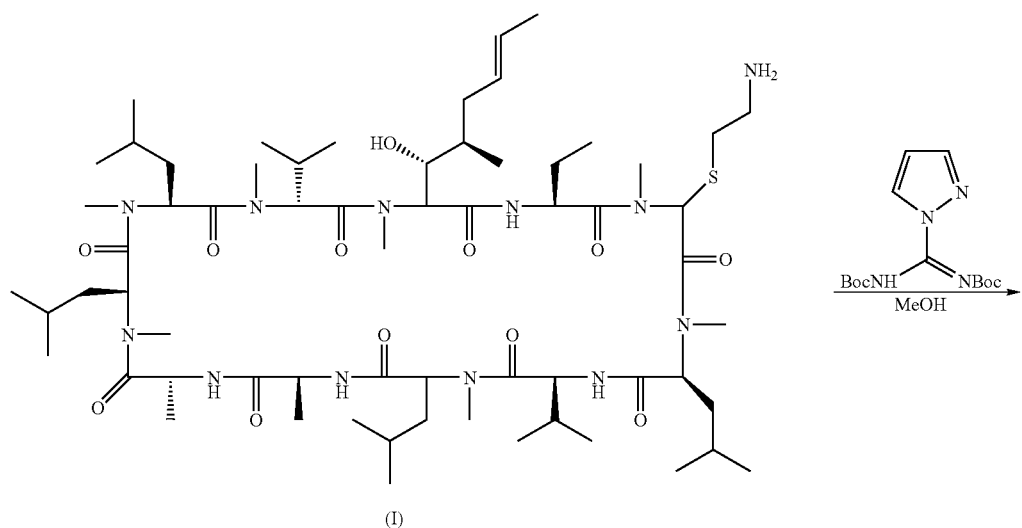
(I)
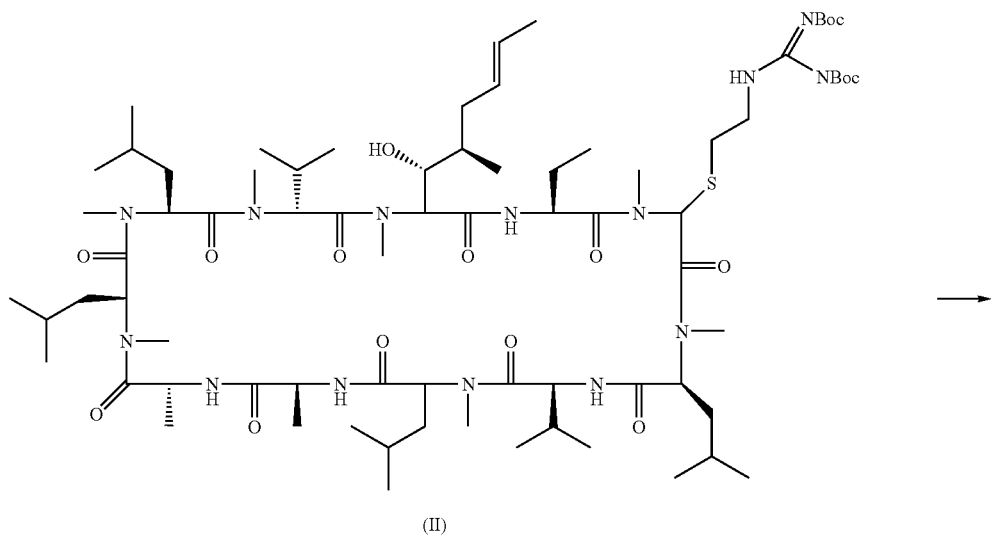
(II)

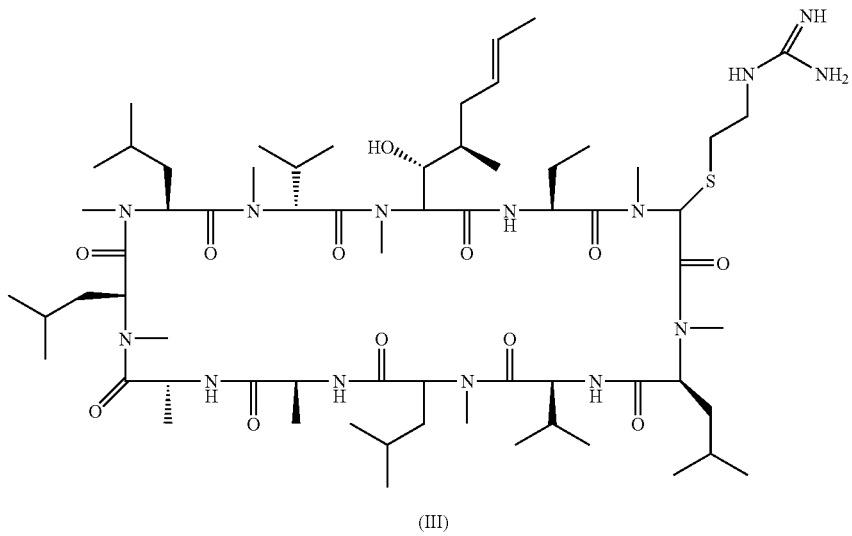

(III)

3-[(2-Guanidyl)-ethylthio]-cyclosporin A (III)

To a solution of 3-[(2-aminoethylthio]-cyclosporin A*-(I)) (200 mg, 0.16 mmol) in methanol (20 mL) was added di-tBoc-pyrazole carboxamidine (250 mg, 0.8 mmol), and the reagents were stirred together for 18 h. After this time, a further portion of the di-Tt-pyrazole carboxamidine (100 mg, 0.32 mmol) was added and the reaction was stirred for a further 3 h. The reaction was then reduced in vacuo, redissolved in dichloromethane, washed with 0.5M citric acid, and the organic layer was dried over $MgSO_4$ and reduced in vacuo. The product was then purified by chromatography column on a 10 g SPE cartridge eluting with diethyl ether to isolate 90 mg (40%) of desired product (II).

As the first member of the Guanidine and Amidine examples synthesized and because of the difficulties anticipated in characterising the final product (III), it was decided to fully and extensively characterize the di-tBoc protected guanidine (II) at this stage and to then take this material onto the free guanidine (III) by acid hydrolysis. Subsequent analogues in this Guanidine and Amidine subclass made from 3-[(2-aminoethylthio]-cyclosporin A were then characterised principally by MS Compound (II) was analysed by $^1H$, $^{13}C$, DEPT NMR and subsequently by a series of 2-D NMR experiments, HMQC, HMBC and DEPT-HMQC.

Presence of the 3-[(2-Guanidyl)-ethylthio]side chain was confirmed by 1D & 2D NMR. Analysis was performed in $CDCl_3$ solution at 300K on a Bruker DRX500 spectrometer.

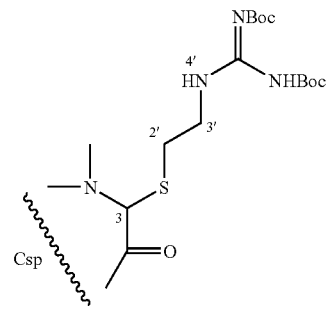

$^1H$ NMR Key Resonances:
  δ=1.50, 1.51 ppm (2 singlets, 2×Boc, 18H, 6×$CH_3$)
  δ=5.89 ppm, (singlet, sarcosine, 1H)
2D Spectra
  Using $^1H$ detected Hetronuclear Multiple Quantum Coherence (HMQC), Hetronuclear Multiple Bond Correlation (HMBC) and edited Hetronuclear Single Quantum Coherence (DEPT-HSQC) experiments, connectivity and assignment may be made confirming the presence of the 3-[(2-Guanidyl)-ethylthio]side chain.
  H (3) to 2' (multiplet, $^1H$ 2.84 ppm, 2H).
  2' to 3' (multiplet, $^1H$ 3.67 ppm, 2H).
  3' to NH 4' (triplet $J_{HH}$ 5.8 Hz, $^1H$ 8.67 ppm, 1H).
  To a solution of the di-tBoc protected 3-[(2-Guanidyl)-ethylthio]-cyclosporin A (II) (21 mg, 0.0138 mmol) in dichloromethane (0.3 mL) was added trifluoroacetic acid (0.3 mL) and the solution was stirred at room temperature for 1 hour. The solution was concentrated to give the product (III) as a white solid (20 mg; 100%)
  Analysis by MS ($E^+$) showed a mass of 1320.2 (M+H) consistent with the proposed structure

EXAMPLE 2

3-[(2-N,N-dimethylformamidinyl)-1-thioethyl]-cyclosporin A (III)

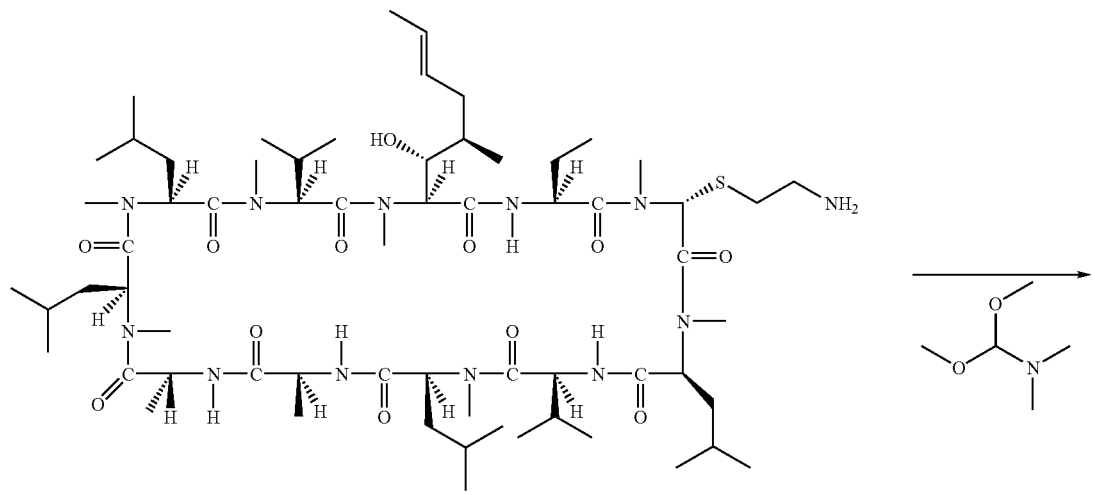

$C_{64}H_{116}N_{12}O_{12}S$
Exact Mass: 1276.86
Mol. Wt.: 1277.74

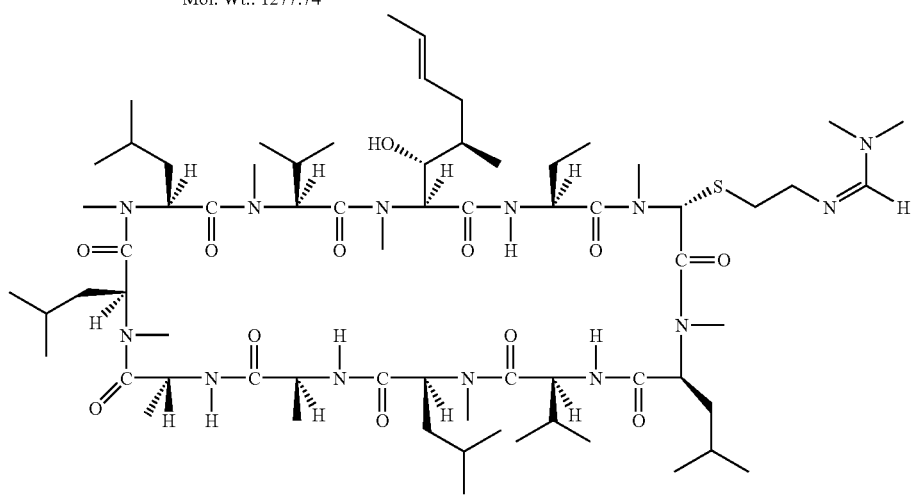

$C_{67}H_{121}N_{13}O_{12}S$
Exact Mass: 1331.9
Mol. Wt.: 1332.82

A mixed solution of 3-(1-thioethylamine)cyclosporine A (0.64 g, 0.5 mmol) and N,N-dimethylformamide dimethyl acetal in 20 mL of THF was refluxed for two hours. After removal of solvent under vacuum, the residue was subject to silica gel column using methylene/methanol (10:1) as eluents, 300 mg of pure product was obtained (yield: 45.0%)

MS (E+) showed a mass of 1332.82 (M+H$^+$) consistent with the proposed structure.

Other methods will be apparent to a chemist skilled in the art as will methods for preparing starting materials and intermediates etc In accordance with the present invention, the cyclosporin A derivatives may be applied to an affected eye in any efficacious concentration, e.g., 0.01 to saturation (e.g. greater than 20 weight percent) in a pharmaceutically acceptable excipient. From 0.01 to 50 weight percent, preferably from 0.1 to 20 weight percent, of cyclosporin A derivatives in a pharmaceutically acceptable excipient may be used. Such pharmaceutically acceptable excipients are, for example, animal oil, vegetable oil, an appropriate organic or aqueous solvent, an artificial tear solution, a natural or synthetic polymer, or an appropriate membrane to encapsulate the cyclosporin A derivative.

Specific examples of these pharmaceutically acceptable excipients are olive oil, arachis oil, castor oil, mineral oil, petroleum jelly, dimethyl sulphoxide, chremophor, Miglyol 182 (commercially available from Dynamit Nobel Kay-Fries Chemical Company, Mont Vale, N.J.), an alcohol (e.g. ethanol, n-propyl alcohol, or iso-propyl alcohol), liposomes or liposome-like products or a silicone fluid. Preferred excipients are dimethyl sulphoxide and olive oil. Mixtures of at least two of any suitable excipients may be used.

Examples of artificial tear excipients which can be advantageously used in the practice of this invention are isotonic sodium chloride, cellulose ethers such as hydroxypropylmethylcellulose and hydroxyethylcellulose, polyvinyl alcohol and available artificial tea solutions.

An example of a useful polymeric excipient is a polyoxyethylated castor oil.

Examples of pharmaceutically acceptable membranes which can be advantageously used in the practice of this invention are microdone, an artificial lipid membrane, polyvinyl alcohol, or methylcellulose.

The cyclosporin A derivatives are advantageously administered topically as an ophthalmic drop (solution or suspension) or ophthalmic ointment containing an effective amount of the derivative. Concentrations of 0.01 to 50 weight percent, preferably 0.1 to 20 weight percent, of the cyclosporin A derivatives are used in the practice of the present invention.

In accordance with a method of the present invention, at least one of the cyclosporin A derivatives is administered topically in any quantity required to provide the degree of treatment needed. For example, 5 microliters to 1 milliliter of a solution, suspension, or ointment containing an effective amount of the cyclosporin A derivative, such as 0.01 to 50 weight percent, preferably 0.1 to 20 weight percent, of the cyclosporin A derivative is advantageously used.

Numerous advantages accrue with the practice of the present invention. The method of the present invention is useful in that it can locally prevent activation of a presystemic response. Topical administration of the cyclosporin A derivatives to a patient's tear deficient eye increases tear production in the eye. Thus, such treatment further serves to correct corneal and conjunctival disorders exacerbated by tear deficiency and KCS, such as corneal scarring, corneal ulceration, inflammation of the cornea or conjunctiva, filamentary keratisis, mucopurulent discharge and vascularization of the cornea. Furthermore, the cyclosporin A derivatives directly decrease the immune response and granulation and neovascularization.

Further objects of this invention, together with additional features contributing thereto and advantages accruing therefrom will be apparent from the following examples of the invention.

The foregoing description details specific methods and compositions that can be employed to practice the present invention, and represents the best mode contemplated. Thus, however detailed the foregoing may appear in text, it should not be construed as limiting the overall scope hereof; rather, the ambit of the present invention was to be governed only by the lawful construction of the appended claims. In particular, although the method of the present invention has been described with the use of the specific cyclosporine A derivatives of the above formula, the novel cyclosporine derivatives that may be used in the method of the present invention further include 3-substituted iminoalkylthio cyclosporin A derivatives, preferably 3-substituted diaminoiminoalkylthio cyclosporin A derivatives, e.g. ((R)-(diamino)iminoalkylthio-Sar)$^3$-(4'-hydroxy-MeLeu)$^4$ cyclosporin A, ((R)-(alkyl)(dialkylamino)iminoalkylthio-Sar)$^3$-(4'-hydroxy-MeLeu)$^4$-cyclosporin A, ((R)-(alkyl)(dialkylamino)iminoalkylthio-Sar)$^3$-cyclosporin A derivatives and ((R)-(diamino)iminoalkylthio-Sar)$^3$-cyclosporin A derivatives.

What is claimed is:

1. A compound selected from the group consisting of compounds represented by the formula:

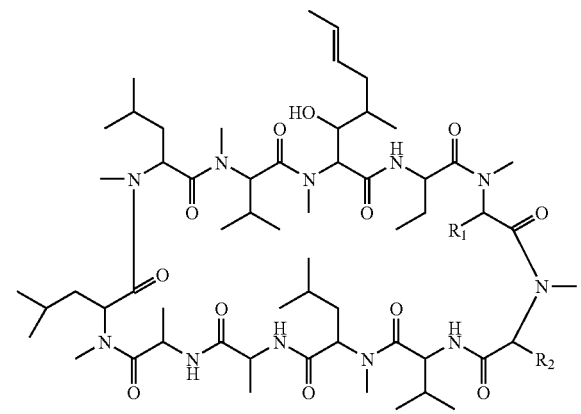

wherein $R_1$ is S-Alk-R wherein Alk is an alkylene or alkylenyl linkage, R is —N=C(NR$_3$R$_4$)(NR$_5$R$_6$) or —NR$_7$[(NR$_3$R$_4$)C=NR$_5$], or —N=C(R$_8$)(NR$_9$R$_{10}$), wherein
$R_3$ is H,
$R_4$ is H,
$R_5$ is H,
$R_6$ is H,
$R_7$ is H,
$R_8$ is H,
$R_9$ is H or methyl,
$R_{10}$ is H or methyl,
and $R_2$ is selected from the group consisting of hydroxyl, alkyl of from 1 to 7 carbon atoms, and hydroxyl-substituted alkyl of from 1 to 7 carbon atoms.

2. The compound of claim 1 wherein Alk is a methylene or a $C_2$ to $C_6$ polymethylene linkage.

3. The compound of claim 1 wherein Alk is a $C_3$ to $C_6$ alkenylenyl linkage.

4. The compound of claim 1 wherein said compound is selected from the group of compounds according to claim 1 wherein $R_1$ is —S(CH$_2$)$_2$N=C(NH$_2$)$_2$ and $R_2$ is —CH$_2$CH(CH$_3$)$_2$, —CH$_2$C(OH)(CH$_3$)$_2$, —CH(CH$_3$)$_2$ or —CH(CH$_3$)CH$_2$CH$_3$.

5. A compound that is 3-[(2-Guanidyl)-ethylthio]-cyclosporin A.

6. A compound that is 3-[(2-N,N-dimethylformamidinyl)-1-thioethyl]-cyclosporin A.

* * * * *

UNITED STATES PATENT AND TRADEMARK OFFICE
CERTIFICATE OF CORRECTION

PATENT NO.       : 8,716,238 B2
APPLICATION NO.  : 12/499911
DATED            : May 6, 2014
INVENTOR(S)      : Michael E. Garst It is certified that error appears in the above-identified patent and that said Letters Patent is hereby corrected as shown below:

On the title page, item (56), under "Other Publications", in column 1, lines 2-3, delete "infiammtory" and insert -- inflammatory --, therefor.

On the title page, item (56), under "Other Publications", in column 1, line 5, delete "Atropic" and insert -- Atrophic --, therefor.

On the title page, item (56), under "Other Publications", in column 2, line 4, delete "Thesarcosine" and insert -- the Sarcosine --, therefor.

On the title page, item (57), under "Abstract", in column 2, line 13, delete "R is R is" and insert -- R is --, therefor.

In the Specification

In column 3, line 7, delete "chorioentinitis," and insert -- chorioretinitis, --, therefor.

In column 3, line 21, delete "uveitities." and insert -- uveitis. --, therefor.

In column 3, line 26, delete "autoinmmune" and insert -- autoimmune --, therefor.

In column 4, line 5, delete "derivatives" and insert -- derivatives. --, therefor.

In column 11, line 1, delete "WO/2003/051797N," and insert -- WO/2003/051797 N, --, therefor.

In column 15, line 56, delete "MS" and insert -- MS. --, therefor.

In column 16, line 65, delete "100%)" and insert -- 100%). --, therefor.

In column 16, line 67, delete "structure" and insert -- structure. --, therefor.

In column 17, line 57, delete "45.0%)" and insert -- 45.0%). --, therefor.

In column 17, line 62, delete "etc" and insert -- etc. --, therefor.

In column 18, line 58, delete "chremophor," and insert -- cremophor, --, therefor.

In columns 19-20, line 54 (Col. 19) and 1 (Col. 20), delete "iminoalkyllthio" and insert -- iminoalkylthio --, therefor.

Signed and Sealed this
Second Day of September, 2014

Michelle K. Lee
*Deputy Director of the United States Patent and Trademark Office*